(12) United States Patent
Briggs

(10) Patent No.: US 8,356,847 B1
(45) Date of Patent: Jan. 22, 2013

(54) HAND-HELD TYPING AID

(76) Inventor: Kenya Marie Briggs, San Francisco, CA (US)

(*) Notice: Subject to any disclaimer, the term of this patent is extended or adjusted under 35 U.S.C. 154(b) by 745 days.

(21) Appl. No.: 12/586,928

(22) Filed: Sep. 30, 2009

Related U.S. Application Data

(60) Provisional application No. 61/198,288, filed on Nov. 4, 2008.

(51) Int. Cl.
*B43L 15/00* (2006.01)
*B25B 33/00* (2006.01)

(52) U.S. Cl. ........................................................ 294/25

(58) Field of Classification Search ................ 294/25, 294/3.5, 15, 26, 165, 218; 16/422; 401/6, 401/8, 131; 15/433; 623/65
See application file for complete search history.

(56) References Cited

U.S. PATENT DOCUMENTS

| | | | | |
|---|---|---|---|---|
| 2,866,440 A | * | 12/1958 | Green ............................ | 401/8 |
| 3,934,877 A | * | 1/1976 | White .......................... | 463/47.5 |
| 4,340,374 A | * | 7/1982 | Culley .......................... | 434/201 |
| 4,386,448 A | | 6/1983 | Kohn | |
| 4,462,593 A | * | 7/1984 | Carty, Jr. ...................... | 463/47.5 |
| 5,120,261 A | * | 6/1992 | Dietzman ..................... | 446/473 |
| 5,306,193 A | * | 4/1994 | Yang ............................. | 446/215 |
| 5,779,292 A | | 7/1998 | Kasday | |
| 2001/0007392 A1 | * | 7/2001 | Sugarman ...................... | 294/25 |
| 2007/0228092 A1 | | 10/2007 | Hammermeister | |
| 2010/0289282 A1 | * | 11/2010 | Avery et al. ..................... | 294/25 |

OTHER PUBLICATIONS

Schofield, Access, Design and Technology, ParaQuad News, Aug. 2008, Issue 3, pp. 8 (image) and 9 (text), Silverwater, DC Australia.
Rehabilitation Engineering Research Center on Technology Transfer Product Resource Directory, p. 13. "Wanchiks Typer Orthosis," Center for Assistive Technology, University at Buffalo, Buffalo, NY.

* cited by examiner

*Primary Examiner* — Paul T Chin

(57) ABSTRACT

One embodiment of a typing aid (1) of the type having two identical halves, or identical typing units (10) and (11), which are attached to one another with a flexible attachment device (6). Each said identical typing unit consists of a protruding segment (4), an impact tip (5), one or more anchoring devices (3) and a gripping appendage (2) assembled so that said protruding segment and said impact tip extend away from the base of said gripping appendage. Other embodiments are described and shown.

10 Claims, 7 Drawing Sheets

HAND-HELD TYPING AID

CROSS-REFERENCE TO RELATED APPLICATIONS

This application claims the benefit of Provisional Patent Application No. 61/198,288, filed on Nov. 4, 2008 by the present inventor, which is incorporated by reference.

BACKGROUND

1. Field of Invention

This invention relates to typing aids, specifically to hand-held typing aids for people who experience injury or discomfort in their hands or arms when typing on a keyboard apparatus, or who wish to avoid same.

2. Prior Art

It is estimated that one in every four people who type in the United States suffers from repetitive stress injury (RSI). Many of these individuals experience mild-to-severe discomfort in their hands or arms from the act of repeatedly depressing the keys of a computer keyboard, typewriter, calculator, cash register, etc. with their fingers (as opposed to those, for example, who experience physical discomfort while using a computer mouse). Some of these individuals are able to reduce their discomfort or heal their injuries through physical therapy and improved typing posture. Others seek relief through surgery. Still others stop typing altogether, switching careers or leaving employment and filing for disability insurance. Many continue to work, utilizing typing aids to contain or minimize their discomfort or injury.

Currently, typing aids fall into three categories: ergonomic keyboards, voice-activated software, and hand-held typing aids. Ergonomic keyboards such as Microsoft's wave-shaped Natural Keyboard Elite™ or the Kinesis® Freestyle™ adjustable split keyboard require the use of fingers and can therefore aggravate existing RSI in the hands and arms. Voice-activated typing software, such as ScanSoft's Dragon NaturallySpeaking™ speech recognition software, relieve the hands and fingers but limit the user to computers running said software, are prone to hard-to-locate text errors, and are less useful for people working in noisy environments or those working in close proximity to others. Hand-held typing aids, like the Slip-On Typing/Keyboard Aid, by AdLib, Inc. (not patented), and Wanchik's Typer Orthosis (not patented), force the hands and arms into a non-neutral position and direct typing pressure to a single finger, causing stress to the tendons and nerves serving that finger. The Keyboard Aid/Button Pusher, by Maddak, Inc. (not patented), also promotes a non-neutral hand and arm position. U.S. patents 2007/0228092 A1 to Hammermeister (2007) and U.S. Pat. No. 5,779,292 to Kasday (1998) orient the user's hands and arms into a neutral position. However, these typing aids are secured to the user's palms, which can make them challenging to remove, rendering them less useful in fast-paced work environments where hands must be quickly freed to answer phones, jot down notes, etc. U.S. Pat. No. 4,386,448 to Kohn (1983) promotes a neutral hand position by way of a spherical grip into which various tools may be inserted. However, the grip is cumbersome to hold, obscures areas of the keyboard from the user's view, does not provide a neck cord for easy access, and can roll out of the user's reach when laid down on a desk or table.

SUMMARY

In accordance with one embodiment, my hand-held typing aid comprises two identical typing units each having a gripping appendage, a protruding segment and an impact tip. The identical typing units are fastened together with a cord or flexible attachment device.

DRAWINGS

Figures

In the drawings, closely related figures have the same number and different alphabetical suffixes.

DRAWINGS

Reference Numerals

Figure 1A:
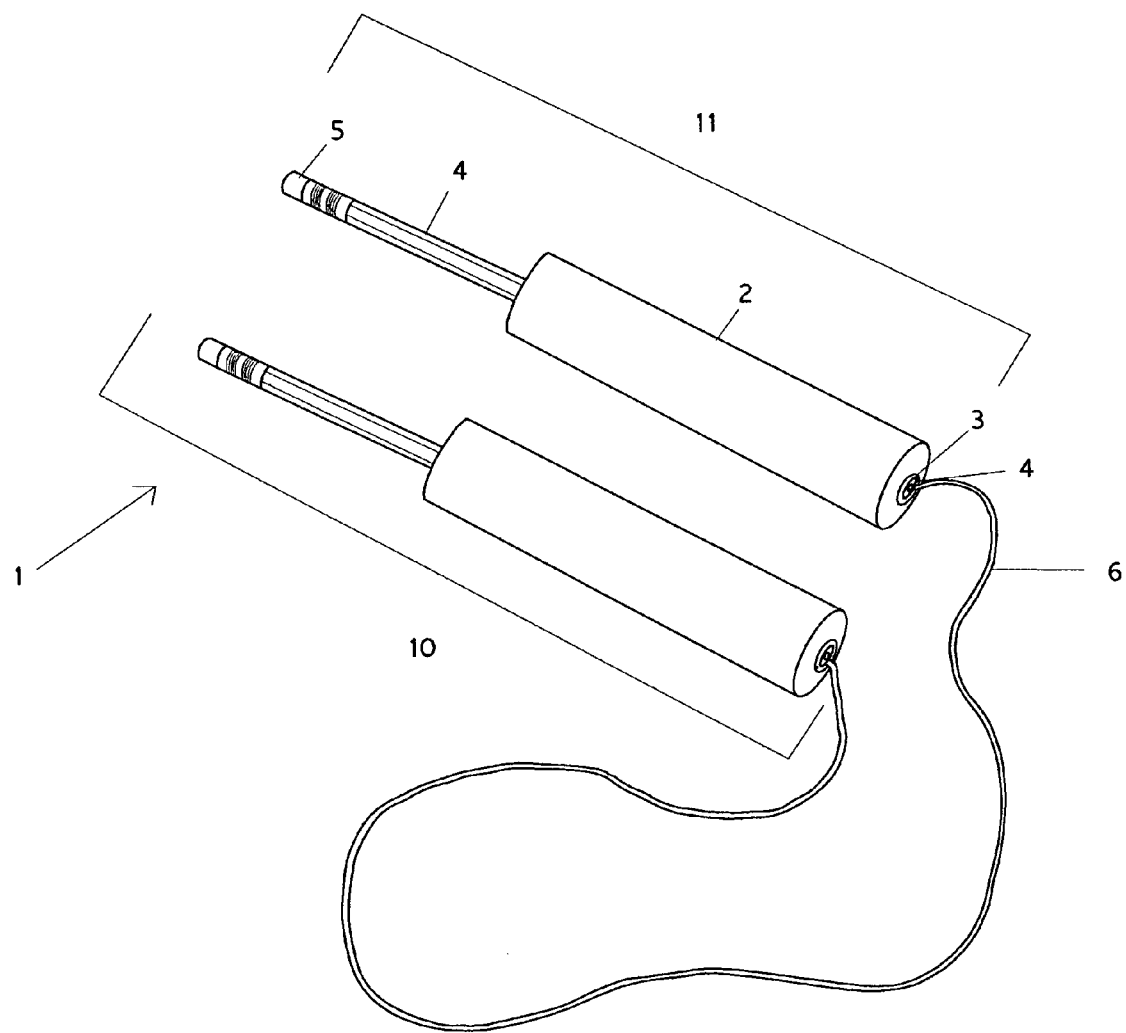
FIGS. 1A to 1H show various views of a manual typing aid supplied with gripping appendages, protruding segments, impact tips, anchoring devices and a flexible attachment device in accordance with one embodiment.
Figure 1B:
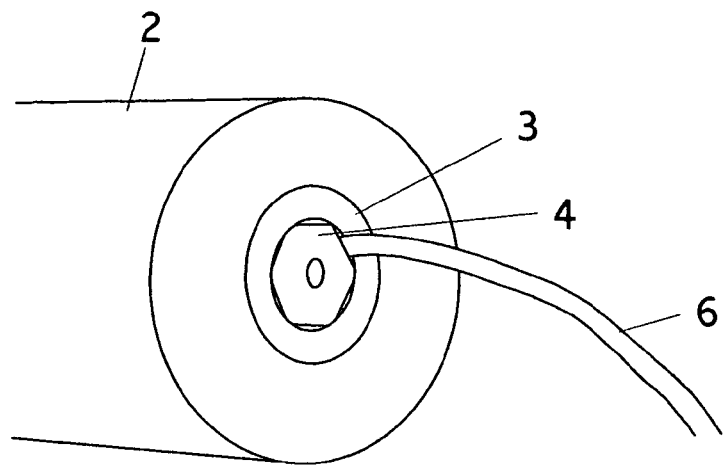

1 Typing aid
2 Gripping appendage
3 Anchoring device
4 Protruding segment
5 Impact tip
6 Flexible attachment device
7 Interior channel
8 Connecting agent
9 Inverted groove
10 One identical typing unit
11 The other identical typing unit

DETAILED DESCRIPTION

FIGS. 1A to 1F

Preferred Embodiment

One embodiment of the typing aid 1 comprises two identical halves or identical typing units 10 and 11, which are fastened together with a flexible attachment device 6 (FIG. 1A). Each unit consists of one protruding segment 4 (equipped with an impact tip 5), one or more anchoring devices 3, and one gripping appendage 2 (provided with an interior channel 7) (FIG. 1D).

Figure 1C:
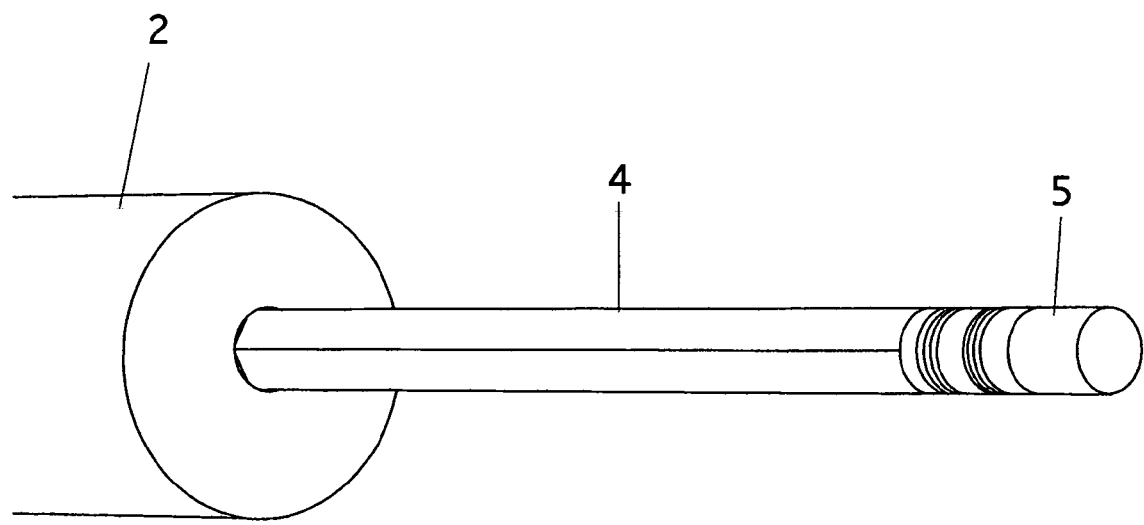
Figure 1D:
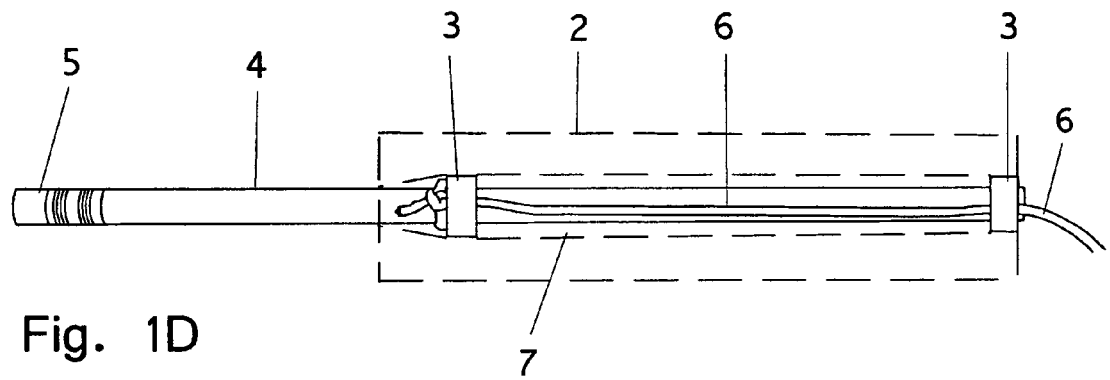

The protruding segment (4) used in this embodiment is an unsharpened, standard-sized pencil equipped with an attached eraser, which acts as an impact tip 5 (FIG. 1C). However, any light, stiff, rod-shaped structure such as a wooden dowel or aluminum rod can be substituted for the pencil, and any friction-causing or elastomer material, such as a liquid rubber coating or a removable rubber eraser, can be used as an impact tip. In addition, rigid rubber or silicon rods may be used as protruding segments, and their silicon/rubber ends would act as impact tips.

Figure 1E:
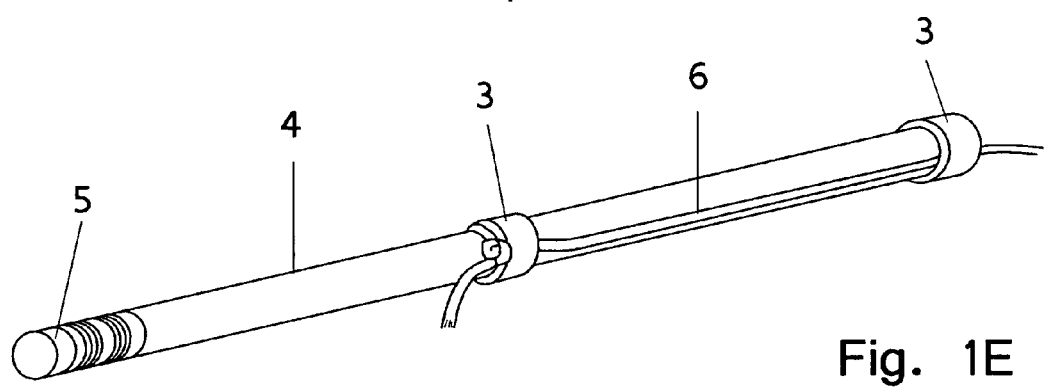
Figure 1F:
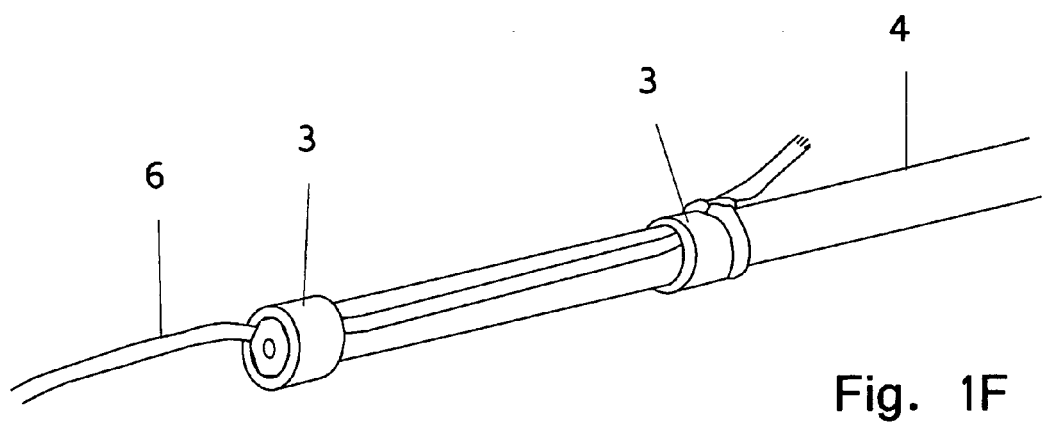

One end of a flexible attachment device 6 is tied around the mid-section of a protruding segment 4, and is secured to this location with an anchoring device 3. The loose end of the flexible attachment device extends up the length of the protruding segment and is secured at its uppermost end (the end opposite the impact tip) with a second anchoring device (FIGS. 1E and 1F). This process is repeated on the remaining end of the flexible attachment device so that two protruding segments are attached to opposite ends of the flexible attachment device.

The flexible attachment device utilized in this embodiment is a length of satin cord sized 1 mm in diameter and approximately 34 inches long (available at Michaels Art Supplies, headquartered in Irving, Tex.). However, different materials suitable to wear around the neck are possible, such as nylon, cotton, or leather. Additionally, a cord of wider or narrower diameter can also be used so long as it will thread between the anchoring device and the protruding segment and is strong enough to tolerate the rigors of being repeatedly pulled on and off the neck. A longer or shorter cord can be utilized depending upon the size of the neck and shoulders of the user. Additionally, a small loop can be tied at the center of the cord, once it is attached to the typing aid, to shorten its length.

The anchoring device utilized in this embodiment is a ⅜" segment of ¼" vinyl irrigation or aquarium tubing (available at many gardening and pet supply stores). Other structures, such as a metal staple, can also be used to anchor the flexible attachment device to the protruding segment, so long as said structures fit beneath the gripping appendage 2 (which is described below).

A gripping appendage 2, provided with an interior channel 7, slides over the first protruding segment and accompanying anchoring devices so that the top end of the gripping appendage is flush with the top ends of the protruding segment and upper anchoring device, and the bottom end of the gripping appendage covers the bottom-most anchoring device (FIG. 1D). This process is repeated for the second protruding segment so that both attached protruding segments, and their accompanying anchoring devices, are seated within gripping appendages (FIG. 1A).

The gripping appendages used in this embodiment are tube-shaped handgrips manufactured from NPVC foam, and are available at Grab On Grips, LLC of Walla Walla, Wash.— but other materials such as silicon, cork, rubber, wax, or wood can also be used. Similarly, while the handgrips contemplated for this embodiment are sized 4.25"L×0.375"W×0.250"ID (internal diameter), alternative sizes and shapes, such as contoured handgrips (FIG. 2A), are also possible.

OPERATION

Figure 1G:
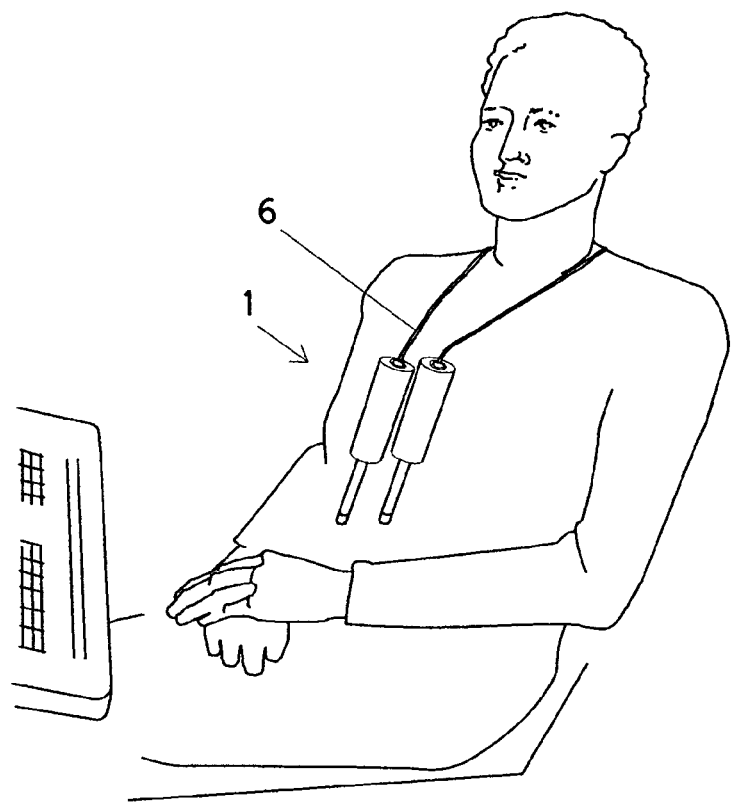
Figure 1H:
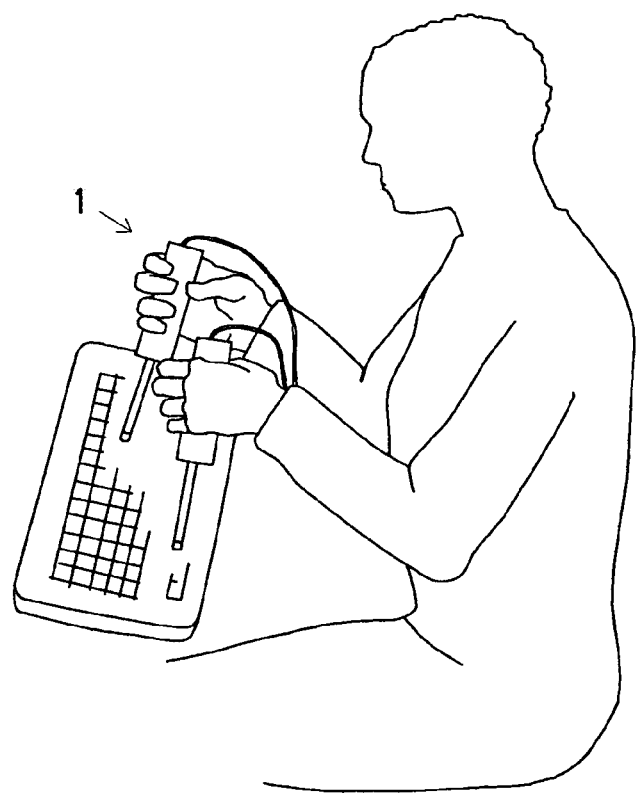

FIGS. 1G and 1H

Preferred Embodiment

The manual typing aid is utilized in the following manner: The user holds a gripping appendage 2 in each hand with the impact tips 5 hovering about an inch over a keyboard apparatus (the impact tips provide friction against the keys of the keyboard apparatus so that the tips of the typing aid accurately strike each key without sliding off). The hands and gripping appendages should be held in a perpendicular orientation to the keyboard so that the flexible attachment device is suspended above the keyboard and in-between the outstretched gripping appendages. The user types by tapping the keys of the keyboard apparatus with the impact tips, using a similar motion to "chipping" ice with an ice pick—only gentler (FIG. 1H). When the user isn't typing or needs to quickly free her hands, she may hang the typing aid around her neck via the flexible attachment device 6 (FIG. 1G). The flexible attachment device can be shortened by tying a simple loop along its length, and can be removed by disassembling the typing aid, unfastening the attachment device from the protruding segments, then re-assembling the aid.

Keyboard users experiencing pain or discomfort in their hands or arms due to typing will find that typing with the manual typing aid does not aggravate their condition. This is because while typing with the typing aid: (a) the user's hands and forearms are rotated into a perpendicular rather than a parallel orientation to the keyboard, which is a healthier and more neutral position for the hands and arms; (b) the user's fingers are stationary and therefore the soft tissues connected to the fingers, such as the tendons and nerves, are not engaged; (c) the repetitive stresses of typing are shifted away from the fingers, hands, and wrists to the larger and more robust muscles of the shoulders and upper arms. In addition, the "chopping" action sustained while typing with the aid is a form of aerobic exercise which strengthens and tones the muscles of the upper arms and shoulders, providing an additional health benefit to the user.

DETAILED DESCRIPTION

FIGS. 2A to 2E

Additional Embodiments

Figure 2A:
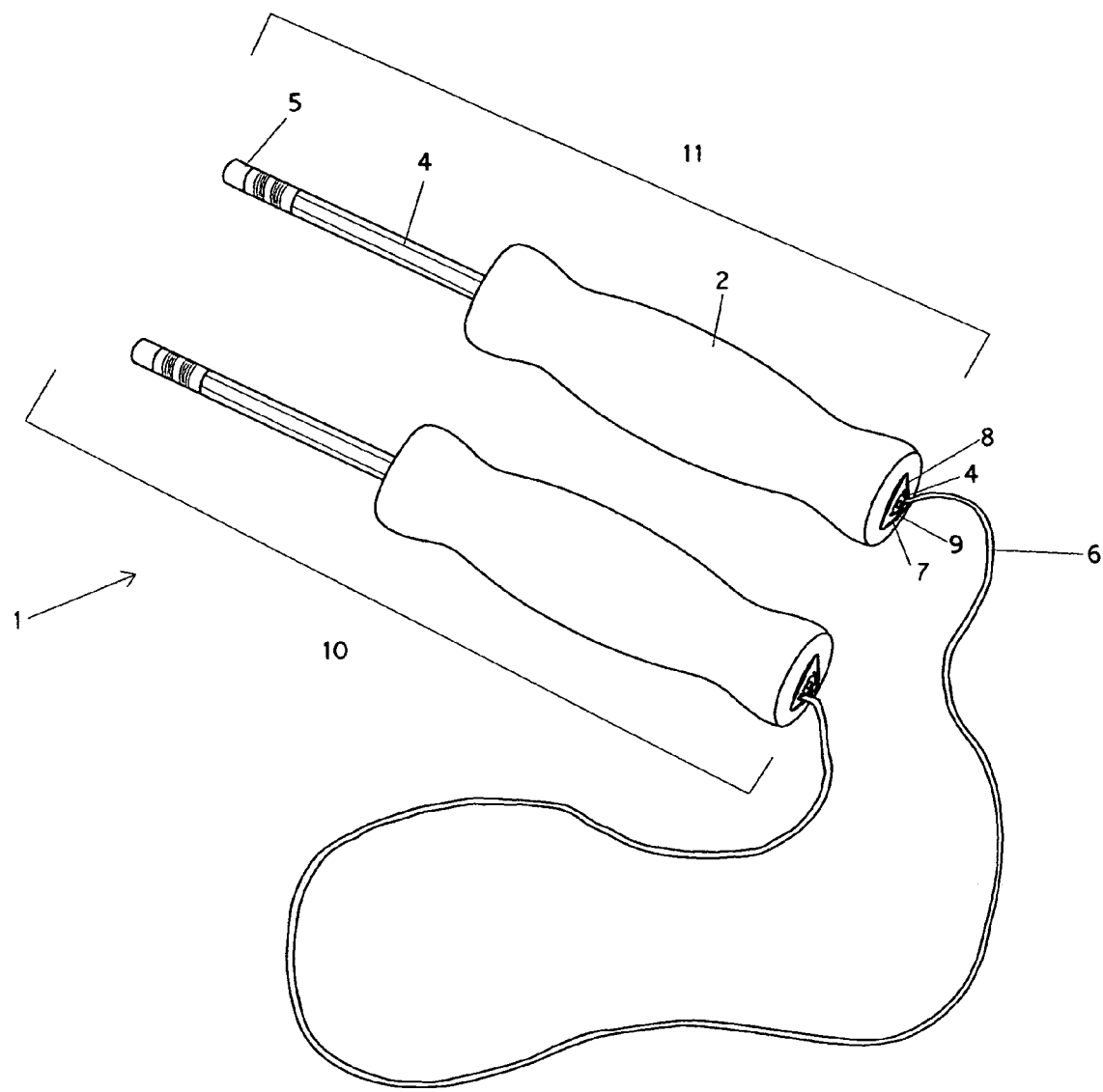
FIGS. 2A to 2E show various views of the typing aid using connecting agents and contoured gripping appendages, in accordance with another embodiment.
Figure 2B:
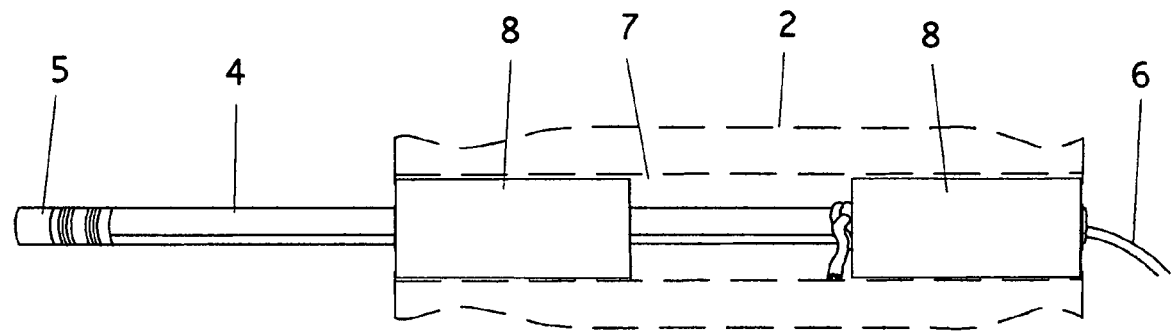
Figure 2C:
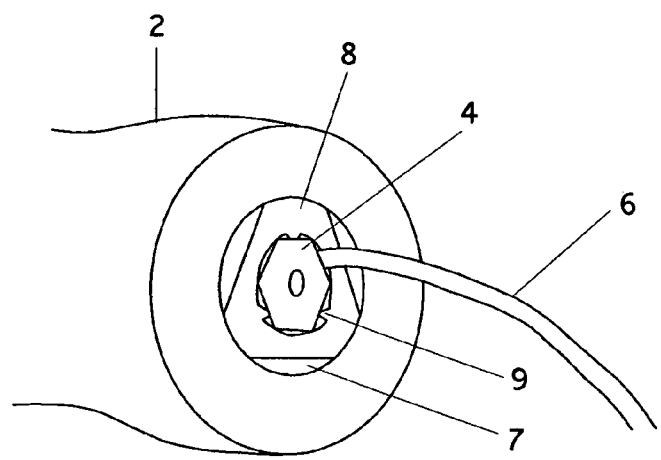
Figure 2D:
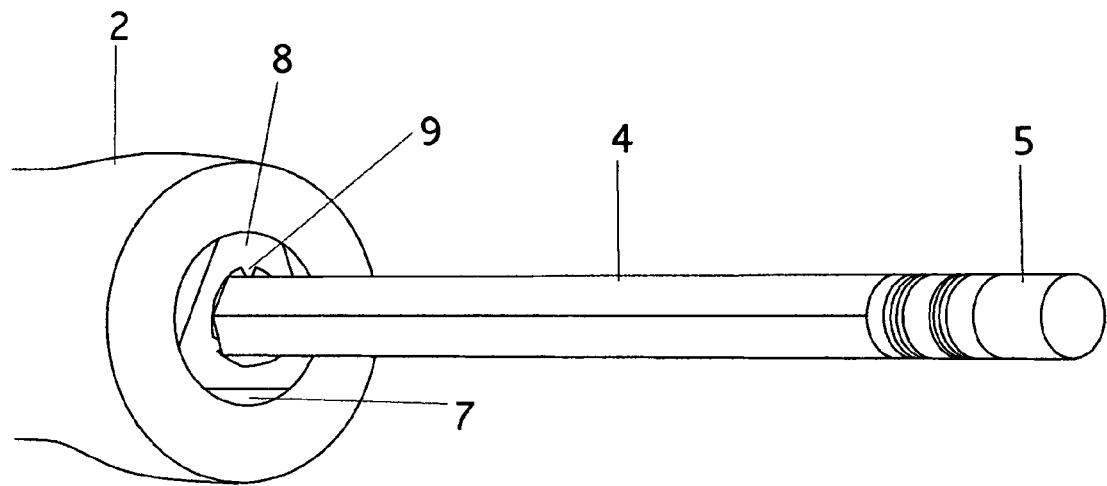
Figure 2E:
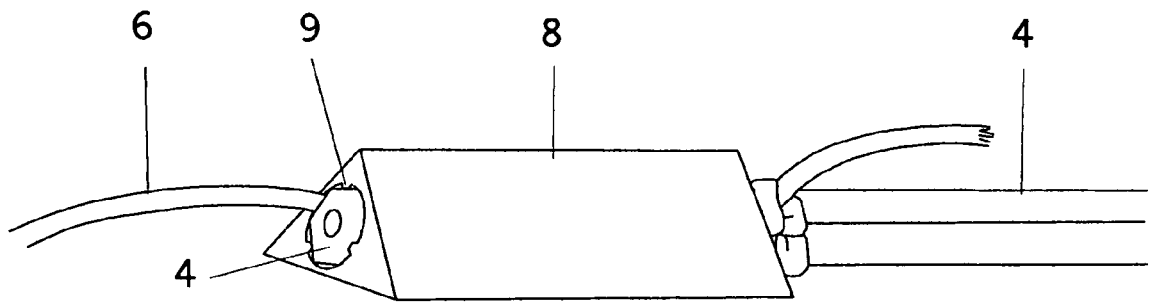

The materials and components used in the manufacture and assembly of the typing aid can vary, as shown in FIGS. 2A-2E. In this embodiment, the anchoring devices are replaced with two standard-sized, triangular pencil grips which are used as connecting agents 8, to join a protruding segment with a gripping appendage having a wider interior channel 7 (FIGS. 2B-2D). Also, in this embodiment, the top-most connecting agent acts as an anchoring device which secures the flexible attachment device to the protruding segment 4 (FIGS. 2B and 2E).

The triangular pencil grips utilized in this embodiment are approximately 1.5"L×⅝"W×⅝"H, are available from Hoyle Products, Inc. of Glenville, Calif., and are equipped with inverted groves 9 which facilitate a tight fit around the protruding segment (FIGS. 2C and 2D). However, different sized or shaped pencil grips or other structures having or not having inverted grooves can also be used so long as they fit snugly around the protruding segment and insert snugly into the interior channel of the gripping appendage. In this embodiment, the connecting agents are spaced approximately one inch apart with the top most connecting agent flush with the top edge of the protruding segment (FIG. 2B).

FIG. 2A shows contoured handgrips, rather than tube-shaped (or cylindrical) hand grips, utilized as gripping appendages.

Advantages

From the preceding description a number of advantages of some embodiments of the manual typing aid become evident:

(a) The user's hands and forearms are aligned in a perpendicular rather than parallel orientation to the keyboard, which is a healthier and more neutral position for the hands and arms.

(b) The user's fingers, hands, and wrists remain stationary while typing with the aid, greatly reducing the likelihood of repetitive stress injury to these appendages.

(c) The stresses of typing are re-directed from the hands to the larger and more robust muscles of the upper arms and shoulders.

(d) The rapid up-and-down aerobic movements sustained by the arms when typing with the typing aid strengthen and tone the larger muscles of the upper arms and shoulders, providing an additional health benefit to the user.

(e) The typing aid does not require audible speaking, as does voice-activated typing software, so the aid can easily be used in close quarters with co-workers.

(f) The optional flexible attachment device keeps the typing aid close yet out-of-the-way, so the user can be typing one moment and "hands-free" the next.

(g) The ability to keep the typing aid close-at-hand coupled with the ease with which the aid may be grasped and released by the user renders the typing aid more compatible with multi-tasking and day-to-day office work than other hand-held typing aids.

(h) The gripping appendages utilized in the preferred and additional embodiments are light-weight, easy to hold and don't slip.

(i) The gripping appendages utilized in the preferred and additional embodiments are one-size-fits-all, and are of such compact proportion that they do not block the keys of the keyboard from the user's view while in use.

(j) The typing aid is extremely simple to use just aim and tap.

(k) The flexible attachment device makes the typing aid extremely portable, so a user can move between several computer stations and always have it handy.

(l) With the exception of the gripping appendage, the components of the typing aid are readily available on the retail market and can be easily replaced by the user, sparing the user from having to purchase a brand new model of the typing aid when a single component (for example, the impact tip) wears out.

(m) The typing aid is inexpensive to produce, making it one of the least-expensive typing aids available.

CONCLUSION, RAMIFICATIONS, AND SCOPE

Accordingly, the reader will see that the manual typing aid in its various embodiments is lightweight, portable, easy to hold, very easy-to-use, and is handy to the user owing to its detachable flexible attachment device which keeps the typing aid close-yet out-of-the-way. In addition, my typing aid is much less expensive and is more practical and easy-to-use in many business settings than are other typing aids currently on the market. Moreover, my typing aid successfully re-routes the repetitive stresses of typing away from the relatively fragile muscles and soft tissues of the hands and fingers to the larger and more robust muscles of the upper arms and shoulders. This ensures that users experiencing pain and discomfort in their hands and arms from typing due to RSI, arthritis, or other causes will not aggravate their injuries while using the typing aid. Additionally, typing with my typing aid is an aerobic exercise, allowing the user to tone her upper arm and shoulder muscles while working.

Furthermore, this manual typing aid has additional advantages in that:
- It accommodates the use of a variety of gripping appendages of different compositions, shapes, sizes and colors including NPVC foam handgrips;
- Its flexibility of design allows for the use of anchoring devices or connecting agents of different shapes and sizes;
- It accommodates a protruding segment that can be a variety of materials and sizes, including a standard pencil;
- It provides the option of using a flexible attachment device or not;
- It allows for personalization by the user by offering gripping appendages, protruding segments, and flexible attachment devices in a variety of colors.

Although the above description contains many different specificities, these should not be construed as limiting the scope of the embodiment but as merely providing illustrations of some of the presently preferred embodiments. For example, the gripping appendage can be of a triangular shape rather than a contoured or tube shape, or the impact tip can comprise a wad of silly putty, wax, etc. rather than a pencil eraser or liquid rubber coating. Thus, the scope of the embodiment should be determined by the appended claims and their legal equivalents, rather than by the examples given.

I claim:

1. A device for interfacing with keys on a keyboard apparatus in the form of a typing aid comprising two identical typing units with each said unit further comprising;
    a gripping appendage which is easily grasped and released by a human hand and which is held within said hand solely by means of said hand's fingers,
    a protruding segment provided at one end with an impact tip and attached at its opposite end to the base of said gripping appendage such that said protruding segment and said gripping appendage form a continuous unit and said impact tip extends away from said gripping appendage, and
    a flexible attachment device comprising a narrow body and two uniform ends with each said end attached to said identical typing units such that said identical typing units are connected to one another and may be worn around a human neck,
    whereby said typing aid isolates said user's fingers from stressful repetitive motion and orients said user's hands in a neutral position relieving typing-related stress in said user's hands and arms, and where further said typing aid may be quickly grasped and released at will and may be hung around said user's neck via said flexible attachment device for easy access.

2. The typing aid of claim 1 wherein said flexible attachment device is secured to said protruding segment component of said identical typing unit via one or more anchoring devices.

3. The typing aid of claim 1 wherein said gripping appendage is provided at its center with an interior channel extending to at least one end of said gripping appendage such that said center of said gripping appendage is hollow and is continuous with the exterior surface of said gripping appendage.

4. The typing aid of claim 3 wherein said protruding segment inserts into said interior channel such that said protruding segment is held firmly in place within said interior channel and said end of said protruding segment containing said impact tip extends away from said gripping appendage.

5. The typing aid of claim 4 wherein one or more connecting agents cling to said protruding segment and cause said protruding segment to hold fast against the surrounding walls of said interior channel such that said connecting agent is sandwiched between said protruding segment and said surrounding walls and firmly holds said protruding segment in place within said interior channel.

6. A method of typing, comprising:
    providing a hand-held typing aid comprising two identical typing units, with each said unit further comprising:
        (a) a gripping appendage which is easily grasped and released by a human hand and which is held within said hand solely by means of said hand's fingers,
        (b) a protruding segment provided at one end with an impact tip and attached at its opposite end to the base of said gripping appendage such that said protruding segment and said gripping appendage form a continuous unit and said impact tip extends away from said gripping appendage,
        (c) a flexible attachment device comprising a narrow body and two uniform ends with each said end attached to said identical typing units such that said identical typing units are connected to one another and may be worn around a human neck, providing a keyboard apparatus, grasping said typing aid by said gripping appendages such that said protruding segments extended downward toward said keyboard apparatus and said impact tips hover one-to-two inches above said keys of said keyboard apparatus, and said flexible attachment device is suspended above said keyboard apparatus and in-between said individual typing units of said typing aid, tapping said keys of said keyboard apparatus with said impact tips of said protruding segments such that individual said keys on said keyboard apparatus are depressed, banging said typing aid around said user's neck via said flexible attachment device when said typing aid is not in use.

7. The method of claim 6 wherein said flexible attachment device is secured to said protruding segment component of said identical typing unit via one or more anchoring devices.

8. The method of claim 6 wherein said gripping appendage is provided at its center with an interior channel extending to at least one end of said gripping appendage such that said center of said gripping appendage is hollow and is continuous with the exterior surface of said gripping appendage.

9. The method of claim 8 wherein said protruding segment inserts into said interior channel such that said protruding segment is held firmly in place within said interior channel and said end of said protruding segment containing said impact tip extends away from said gripping appendage.

10. The method of claim 9 wherein one or more connecting agents cling to said protruding segment and cause said protruding segment to hold fast against the surrounding walls of said interior channel such that said connecting agent is sandwiched between said protruding segment and said surrounding walls and firmly holds said protruding segment in place within said interior channel.

* * * * *